United States Patent [19]

Olah

[11] Patent Number: 4,814,544
[45] Date of Patent: Mar. 21, 1989

[54] ISOMERIZATION OF BUTANE

[75] Inventor: George A. Olah, Beverly Hills, Calif.

[73] Assignee: El Paso Products Company, Odessa, Tex.

[21] Appl. No.: 675,460

[22] Filed: Nov. 28, 1984

Related U.S. Application Data

[63] Continuation of Ser. No. 561,223, Dec. 14, 1983, abandoned.

[51] Int. Cl.$^4$ ............................................. C07C 5/13
[52] U.S. Cl. ..................................................... 585/747
[58] Field of Search ........................................ 585/747

[56] References Cited

U.S. PATENT DOCUMENTS

| | | | |
|---|---|---|---|
| 2,259,723 | 10/1941 | Ballard et al. | 585/731 |
| 2,373,740 | 4/1945 | Birch et al. | 585/734 |
| 2,425,572 | 8/1947 | Slotterbeck | 585/731 |
| 3,231,633 | 1/1966 | Kramer | 585/731 |
| 3,364,280 | 1/1968 | Kramer | 585/730 |
| 3,766,293 | 10/1973 | Parker et al. | 585/731 |
| 3,778,489 | 12/1973 | Parker et al. | 585/730 |
| 3,880,945 | 4/1975 | Kramer et al. | 585/747 |
| 3,887,635 | 6/1975 | Parker et al. | 585/730 |
| 3,922,319 | 11/1975 | Brockington | 585/731 |
| 3,925,318 | 12/1975 | Parker et al. | 585/718 |
| 3,970,721 | 7/1976 | Brockington et al. | 585/731 |
| 3,996,116 | 12/1976 | Herlem et al. | 585/747 |
| 4,033,899 | 7/1977 | Bennett et al. | 585/731 |
| 4,065,516 | 12/1977 | Moser, Jr. et al. | 585/730 |

*Primary Examiner*—John Doll
*Assistant Examiner*—Jeffrey E. Russel
*Attorney, Agent, or Firm*—Fred S. Valles; Margareta LeMaire

[57] ABSTRACT

Normal butane is isomerized to isobutane by means of a catalyst composition consisting essentially of 95 to 99 weight percent fluorosulfuric acid and 1 to 5 weight percent of a protic co-acid selected from the group consisting of hydrogen fluoride, sulfuric acid, trifluoromethanesulfonic acid and mixtures thereof. The isomerization is carried out under low temperatures and at short contact times.

15 Claims, No Drawings

ISOMERIZATION OF BUTANE

This is a continuation of co-pending application Ser. No. 561,223, filed on Dec. 14, 1983, now abandoned.

This application is related to copending applications, Ser. No. 458,825, Ser. No. 458,826 now abandoned and Ser. No. 458,827, now abandoned filed Jan. 18, 1983, which disclose the upgrading of natural gasoline with related catalysts.

BACKGROUND OF THE INVENTION

1. Field of the Invention

The present invention relates to an improved isomerization process. More particularly, the invention concerns the isomerization of butane to isobutane with strong acid catalyst systems at low temperatures and short contact times.

2. Description of the Prior Art

The isomerization of n-butane to isobutane is of substantial practical significance. n-Butane is available from natural gas sources which contain only very limited amounts of the branched chain isomer which is essential in the manufacture of polyisobutylene, tert-butyl alcohol and other products.

The isomerization of n-butane to isobutane is generally carried out by using an acidic catalyst such as aluminum chloride or a supported noble metal catalyst capable of isomerization via dehydrogenation-hydrogenation. Industrial processes operate in the 100°–200° C. temperature range. The two major available processes are the UOP and BP processes. The UOP process operates with a platinum containing catalyst at 250°–380° C. whereas the BP isomerization process uses a platinum catalyst and operates between 15 and 30 atms pressure at a temperature of between about 150°–200° C. Under these conditions, n-butane feed under hydrogen pressure is brought to near equilibrium conversion to isobutane. The liquid product which contains normal butane and isobutane is separated from the cooled reactor effluent gas which is recycled to the reactor with hydrogen makeup. After stabilization, the liquid is passed to the deisobutanizer column from which an isobutane overhead product is taken. The lower product, normal butane, is recycled to the reactor loop. The bottom product from the deisobutanizer is a $C_5+$ reject which can be used as a low octane by-product.

The discoveries of superacidic systems (i.e., acids many million times stronger than 100% $H_2SO_4$ or anhydrous hydrogen fluoride) by G. A. Olah opened up extensive research into superacid catalyzed hydrocarbon conversions, including the isomerization of alkanes. U.S. Pat. No. 3,708,553 and U.S. Pat. No. 3,766,286 disclose processes for the alkylation of hydrocarbons with alkenes and the isomerization of hydrocarbons, respectively, utilizing superacidic catalysts of one or more Lewis acid halides, preferentially fluorides such as antimony pentafluoride, tantalum pentafluoride, niobium pentafluoride, vanadium pentafluoride, titanium tetrafluoride, molybdenum hexafluoride, bismuth pentafluoride, phosphorus pentafluoride, arsenic pentafluoride, and the like, selected from Group IV-B, V and VI-B elements of the Periodic Table and a strong Bronsted acid such as fluorosulfonic acid, trifluoromethanesulfonic acid, and trifluoroacetic acid. Numerous additional patents describe variations of the superacid catalyzed hydrocarbon transformations and include, for example, the following:

U.S. Pat. No. 3,839,489 discloses isomerization of normal paraffinic hydrocarbons having from 4 to 8 carbon atoms with a catalyst system comprising a Group V-B fluoride, such as arsenic or antimony pentafluoride, and trifluoromethanesulfonic acid or hydrogen fluoride under hydrogen partial pressures ranging from 900 to 4000 psig.

U.S. Pat. No. 3,852,184 discloses the isomerization of alkylcyclopentanes in a reforming feed with a catalyst comprising a metal halide and protonic acid wherein the protonic acid/metal halide molar ratio is at least 2:1 and preferably 5:1.

U.S. Pat. No. 3,855,346 discloses a process for the isomerization of $C_4$–$C_7$ normal and branched chain paraffins with a catalyst comprising trifluoromethanesulfonic acid alone or in combination with a metal fluoride of a Group V-B element such as antimony pentafluoride, arsenic pentafluoride and phosphorus pentafluoride.

U.S. Pat. No. 4,144,282 upgrades light naphtha streams using a fluoroalkanesulfonic acid-antimony pentafluoride mixture as a conversion catalyst.

A description of superacids and hydrocarbon transformation reactions, including isomerization, is disclosed in "Superacids" by George A. Olah, G. K. Surya Prakash and Jean Sommer, *Science*, Oct. 5, 1979, Vol. 206, No. 4414.

In the acid catalyzed isomerization of alkanes, n-butane isomerization represents a special and more difficult problem than that of pentanes, hexanes, heptanes, etc. The reason for this is that in the isomerization of n-butane to isobutane the reaction is either bimolecular, in the presence of butanes, or intramolecular, where it must proceed through a primary isobutyl cation, a relatively high energy species, which consequently raises the activation energy of the process. There is, however, no $\beta$-cleavage involved in the $C_4+$ system. In contrast, however, acid catalyzed protolytic cleavage of the $\alpha$ and $\beta$ C—C bonds in n-butane is a serious competing reaction, particularly at high superacidities. This is the reason, for example, why Brouwer et al reported (Rec. Trav. Chim. 87, 1435 (1968)), that the extremely strong 1:1 $HF$-$SbF_5$ system is not isomerizing n-butane to isobutane, but causes only carbon/and hydrogen scrambling and hydrocracking, whereas higher alkanes are readily isomerized. Similarly, the Magic Acid (1:1 $FSO_3H$-$SbF_5$) catalyzed treatment of n-butane results in extensive hydrocracking and only limited isomerization. Oxidative isomerization with $SO_3$ in fluoro- and chlorosulfuric acid, similar to Magic Acid, is disclosed by M. P. Herlem, in French Pat. No. 2,252,351, (CA 84 43277x) but only for alkanes of at least 5 carbon atoms.

SUMMARY OF THE INVENTION

The present invention is directed to the isomerization of n-butane into isobutane by treatment with a liquid catalyst system comprising 95 to 99 weight percent fluorosulfuric acid and 1 to 5 weight percent of a protic co-acid selected from the group consisting of hydrogen fluoride, sulfuric acid, trifluoromethanesulfonic acid, and mixtures thereof. Minor amounts of an initiator conveniently produced in situ by the addition of an olefin to the feed stream permit the isomerization to be carried out at exceedingly short contact times and low temperatures to obtain high conversions to isobutane with minimum formation of cracking and secondary reaction products.

DETAILED DESCRIPTION OF THE INVENTION

The improved butane isomerization process of the invention is based on the discovery that liquid catalyst compositions comprising 95 to 99 weight percent fluorosulfuric acid and 1 to 5 weight percent of a protic co-acid, such as hydrogen fluoride, sulfuric acid, trifluoromethanesulfonic acid or mixtures thereof, preferably in the presence of a suitable activator, are highly effective for catalyzing the isomerization of n-butane to isobutane at low temperatures and extremely short contact times allowing use of a continuous flow system. Conversions of about 70% to isobutane are obtained with minimal production of cracked and secondary reaction products.

The n-butane-isobutane equilibrium is temperature dependent and it is generally accepted that the product composition is determined by this thermodynamic equilibrium. At an operating temperature of 180° C., this represents about 45% isobutane and 55% n-butane, but at −6° C., for example, the equilibrium is 85% isobutane and 15% n-butane. Lowering the temperature thus greatly increases the isobutane component of the equilibrium mixture. In order to obtain a maximum ratio of isobutane over n-butane, it would be advantageous to operate the process at the lowest feasible temperature, but the rates of the isomerization reaction at low temperatures are too slow for practical processes. Also, consideration must be given to the equilibrium of the related carbonium ions and the neutral hydrocarbons in the system. At low temperatures, the thermodynamic equilibrium of the butyl cation is greater than 99.8% for the tertiary-butyl cation and less than 0.2% for the secondary-butyl cation. Accordingly, by means of the present invention, isomerization with the acidic catalyst systems described herein provides a means whereby the isomerization reaction may be carried out at low temperatures and fast reaction rates. n-Butane in excess superacidic media can be completely converted into the tertiary-butyl cation and through it, by hydride abstraction or hydrogenation, into isobutane.

In one embodiment of the invention, fluorosulfuric acid containing 5 weight percent anhydrous hydrogen fluoride is used for isomerization with or without added initiator, such as a butyl fluorosulfate or butyl fluoride. The latter is conveniently formed in situ when small amounts of butylene are added to the acid or hydrocarbon feed. The system is adaptable to hydrogen moderation, which is optional. $HSO_3F$-$SbF_5$ (Magic Acid) and related very strong conjugate superacids are well known as alkane isomerization catalysts. However, even when using hydrogen pressure or a suitable hydrogen donor in the system, such acids cause preferential cracking of n-butane resulting in mixtures of methane, ethane and propane as well as higher hydrocarbons of hydrogen deficient nature. This is indicative that the exceedingly strong superacids prefer C—C bond cleavage and only limited concurrent isomerization to isobutane is obtained. It has been discovered than an efficient way to minimize or eliminate this problem is to use suitable but weaker binary superacids such as fluorosulfuric acid with 1 to 5 weight percent of a protic co-acid such as hydrogen fluoride, sulfuric acid or triflurome-thanesulfonic acid, or mixtures thereof. As shown hereinafter, $FSO_3H$/HF and related compositions were found to be very effective catalysts for obtaining exceedingly fast isomerization rates of n-butane at low temperatures.

The disclosed concentration of 1 to 5 weight percent of protic co-acid is specific to the invention. The relatively small amounts of the co-acid in the catalyst system enhances its activity and also help keep the fluorosulfuric acid active by preventing excessive dissociation. If the amount of co-acid in relation to fluorosulfuric acid is increased, however, the acidity of the system is eventually decreased. A 2:1 weight percent mixture of $FSO_3H$ and HF, for example, is too weak to achieve fast isomerization and has been found to give only 5–7% conversion in batch experiments with a prolonged reaction time. Fluorosulfuric acid with 1 to 5 weight percent HF, however, is very effective and fast isomerization is achieved at low temperature. 10 weight percent already showed significantly decreased activity and the need for prolonged reaction times or more elevated temperature disadvantageous for the process. Thus the definition of the range of HF content is based on experimental data.

The isomerization reaction is carried out by contacting the n-butane charge stock with the catalyst under liquid phase conditions for a period of time sufficient to effect the degree of conversion desired. The length of the contact time depends for the most part upon the temperature employed and the catalyst concentrations employed. The unexpected and extremely efficient isomerizing ability of the above described media is removable. Typical extremely short contact times will range from about 1 second to 30 minutes, preferably from about 30 seconds to 5 minutes.

The mole ratio of catalyst to paraffinic hydrocarbon employed for carrying out the isomerization process of the invention will be in the range of 0.1:1 to 50:1, preferably 0.5:1 to 20:1.

The temperature employed will be in the range of 10° C. to 50° C., preferably 10° C. to 30° C., with pressures sufficient to maintain the hydrocarbon reactant and catalyst as liquid in the reaction zone.

As indicated above, the addition of small amounts of $C_2$–$C_{10}$ olefins, preferably butylenes, to the butane charge stock is desirable and leads to the formation of alkyl fluorides or fluorosulfates whereby an equilibrium concentration of cations is maintained in the system during the isomerization reaction. In the absence of olefins, decreased catalyst activity is observed since the acid catalyst itself serves to form the necessary cation by protolysis-oxidation and is thus slowly consumed. This problem can be minimized by adding a small amount of $C_2$–$C_{10}$ monoolefin, such as butylene, in amounts ranging from 0.05 to 10.0 weight percent, preferably 1 to 5 weight percent, based on the butane feed. Cyclic olefins, such as dicyclopentadiene, may also be used.

The process of the invention can be carried out either in a continuous flow, trickle or batchwise manner, or combinations of treatments may be employed. In the conversion zone, any suitable reactor apparatus which provides thorough contact between the catalyst and the various components of the paraffin feed material, including recycled material, may be used. Since it is particularly important to achieve thorough contact between the catalyst and hydrocarbon mixture, it is contemplated that batch or continuous reactors of the agitator type, the circulator-mixer type, the tower type, or tube reactors with suitable baffles will be used whereby the catalyst is quickly and intimately dispersed throughout the hydrocarbon mixture. The reactor and other apparatus which is in contact with the catalyst should be substantially inert, such as Monel, teflon, aluminum alloys, Hastelloy, etc., so that the catalyst does not react therewith to form substances that either inhibit the isomerization reaction or form excessive amounts of contaminants. This is particularly important in sensitive areas, such as valves, which are exposed to the catalyst.

For commercial reasons, a continuous process is preferred. No special apparatus need be employed and the type of equipment conventionally used for liquid phase polymerization, alkylation, and similar types of equipment may be employed Such process may be employed by using a series of reactors, each equipped as described, in series or in parallel. In a series arrangement, various stages of the isomerization reaction may be carried out in each reactor under conditions of throughput, contact time, amount of catalyst, temperature, etc., best suited for that particular stage.

As noted above, it has been found desirable to carry out the isomerization reaction in the liquid phase at modest temperatures and to efficiently mix the reaction mixture to achieve thorough contact between the catalyst and paraffin. The isomerization process may, if desired, be carried out in the presence of hydrogen which helps suppress side reactions and minimize the amount of hydrocarbon products entering the lower acid or catalyst phase of the reaction mixture. Hydrogen may be introduced into the reaction in an amount sufficient to provide a partial pressure of hydrogen of 100 to 1000 pounds per square inch, preferably 100 to 300 psi. These relatively modest hydrogen pressures substantially suppress side reactions, particularly cracking. Unreacted reactants, catalyst and other products of the reaction can be separated from the desired product and from one another by distillation and returned in whole or in part to the isomerization zone. If desired, a portion of the partially deactivated catalyst can be regenerated or reactivated by any suitable treatment and returned to the isomerization zone.

The following examples illustrate the best mode now contemplated for carrying out the invention without, however, limiting its scope. While the feed material of the examples substantially comprises a purified n-butane hydrocarbon stream, it should be understood, for example, that field butanes or a $C_4$ refinery cut likewise may be isomerized to more highly branched chain paraffins.

EXAMPLES

Example 1

A gaseous stream of butane containing an average of 99% n-butane, was passed through in a continuous fashion a 50 cm long, 2 cm diameter reactor made of stainless steel and charged with 96% (w/w) fluorosulfuric acid and 4% hydrogen fluoride. The temperature was 21° C. and contact time of butane with the acid catalyst was about 30 seconds. The process was operated in a continuous fashion for 48 hours without appreciable change of product composition which was an average of 70% isobutane, 27% n-butane and 3% propane.

Example 2 n-Butane was isomerized as in Example 1 but with an acid catalyst composed of 96% fluorosulfuric acid and 4% sulfuric acid. Product composition was 64% isobutane, 33% n-butane and 3% propane.

Example 3 n-Butane was isomerized as in Example 1 but with an acid catalyst consisting of 95% fluorosulfuric acid, 3% sulfuric acid and 2% hydrogen fluoride. Product composition was 68% isobutane, 29% n-butane and 3% propane.

Example 4

Isomerization was carried out as in Example 1 but with 5% trifluoromethanesulfonic acid. Reaction temperature was 35° C. Product composition obtained was 68% isobutane, 28% n-butane and 4% propane.

Example 5 n-Butane was isomerized as in Example 1 but with an acid catalyst consisting of 95% fluorosulfuric acid, 3% trifluoromethanesulfonic acid and 2% hydrogen fluoride. Product composition was 67% isobutane, 32% n-butane and 2% propane.

What is claimed is:

1. A process for liquid-phase isomerization of normal butane ot isobtuane which consists essentially of contacting normal butane at temperatures less than 50° C. for a period of time less than 30 minutes with a catalyst composition consisting essentially of 95 to 99 weight percent fluoresulfuric acid and 1 to 5 weight percent trifluoromethanesulfonic acid, and thereafter recovering isobutane.

2. A process for liquid-phase isomerization of normal butane to isobutane which consists essentially of contacting normal butane at temperature less than 50° C. for a period of time less than 30 minutes with a catalyst composition consisting essentially of 95 to 99 weight percent fluorosulfuric acid and 1 to 5 weight percent sulfuric acid, and thereafter recovering isobutane.

3. The process of any one of claims 1 or 2 wherein the temperature ranges from 10° C. to 30° C. for a period of time ranging from 30 seconds to 5 minutes.

4. The process of any one of claims 1 or 2 wherein the isomerization is carried out in a continuous manner.

5. The proces of claim 3 wherein a $C_2$-$C_{10}$ olefin is added to the butane charge stock in amounts ranging from aobut 0.05 to 10 percent by weight based on the charge stock for the purpose of providing an equilibrium concentraiton of cations duirng the isomerization reaction and thereby minimizing decreased catalyst activity.

6. The process of claim 4 wherein a $C_2$-$C_{10}$ olefin is added to the butane charge stock in amounts ranging from about 0.05 to 10 percent by weight based on the charge stock for the purpose of providing an equilibrium concentration of cations during the isomerization reaction and thereby minimizing decreased catalyst activity.

7. The process of claim 5 wherein butylene is added to the feedstock in an amount ranging from about 1 to 5 percent by weight.

8. The process of claim 6 wherein butylene is added to the feedstock in an amount ranging from about 1 to 5 percent by weight.

9. A prpocess for liquid-phase isomerization of normal butane to isobutane which consists essentially of contacting butane charge stock and a $C_2$-$C_{10}$ olefin added to the butane charge stock in amouts ranging from about 0.05 to 10% by weight based on the charge stock for the purpose of providing an equilibrium concentration of cations during the isomerization reaction and thereby minimizing decreased catalyst activity at a temperature from 10° C. to 30° C. for a period of time ranging from 30 second to 5 minutes with a catlyst composition consisting essentially of 95 to 99 wt. % fluorosulfuric acid and 1 to 5 wt. % of protic co-acid selected from the group consisting of hydrogen fluoride, sulfuric acid, trifluiormethyanesulfonic acid, and mixtures thereof, and thereafter rcovering isobutane.

10. A continuous process for liquid-phase isomeriation of normal butane to isobutane which consists essentially of contacting butane charge stock and a $C_2$-$C_{10}$ olefin added to the butane charge stock in amounts ranging from about 0.05 to 10% by weight based on the charge stock for the purpose of providing an equilibrium concentration of cations during the isomerization reaction and thereby minimizing decreased catalyst activity at temperature less than 50° C. for a period of time less than 30 minutes with a catalyst composition consisiting essentially of 95 to 99 wt. % fluoresufuric acid and 1 to 5 wt. % of a protic co-acid selected from the group consisting of hydrogen fluoride, sulfuric acid, trifluoromethanesulfonic acid, and mixtures thereof, and thereafter recovering isobutane.

11. The process of claim 9 or 10 wherein in the catlayst is 95 to 99 weight percent fluorsulfuric acid and 1 to 5 weight percent hydrogen fluoride.

12. The process of claim 9 or 10 wherein the catalyst is 95 to 99 weight percent fluorosulfuric acid and 1 to 5 weight percent of a mixutre of hydrogen fluoride and trifluoromethanesulfonic acid.

13. The process of claim 9 or 10 wherein the catalyst is 95 to 99 weight percent fluorosulfuric acid and 1 to 5 weight percent of a mixture of hydrogen fluoride and sulfuric acid.

14. The process of claim 9 wherein butylene is added to the feedstock in an amount ranging from about 1 to 5% by weight.

15. The process of claim 10 wherein butylene is added to the feedstock in an amount ranging from about 1 to 5% by weight.

* * * * *